United States Patent
Puttlitz et al.

(10) Patent No.: US 10,641,664 B2
(45) Date of Patent: May 5, 2020

(54) DISPLACEMENT AND DEFORMATION MONITORING METHOD AND SYSTEM WITHOUT USING ANY STRAIN SENSOR, AND COMPONENTS THEREOF

(71) Applicant: COLORADO STATE UNIVERSITY RESEARCH FOUNDATION, Fort Collins, CO (US)

(72) Inventors: Christian M. Puttlitz, Fort Collins, CO (US); Hilmi Volkan Demir, Ankara (TR); Kevin M. Labus, Fort Collins, CO (US); Kirk C. McGilvray, Fort Collins, CO (US); Emre Unal, Ankara (TR)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

(21) Appl. No.: 16/262,305

(22) Filed: Jan. 30, 2019

(65) Prior Publication Data
US 2019/0162606 A1 May 30, 2019

Related U.S. Application Data

(63) Continuation of application No. PCT/US2018/028590, filed on Apr. 20, 2018.
(Continued)

(51) Int. Cl.
*G01L 1/12* (2006.01)
*G01M 5/00* (2006.01)
(Continued)

(52) U.S. Cl.
CPC .............. *G01L 1/127* (2013.01); *G01L 1/00* (2013.01); *G01L 1/14* (2013.01); *G01M 1/00* (2013.01);
(Continued)

(58) Field of Classification Search
CPC ..... G01L 1/127; A61B 2562/0261; A61B 5/05
See application file for complete search history.

(56) References Cited

U.S. PATENT DOCUMENTS

| 2,356,763 A | 8/1944 | Keinath |
| 3,274,527 A | 9/1966 | Robinson |
| (Continued) | | |

FOREIGN PATENT DOCUMENTS

WO 2005104945 A2 11/2005

OTHER PUBLICATIONS

International Search Report issued in Intl. Appln. No. PCT/US2018/028590 dated Jul. 5, 2018.
(Continued)

*Primary Examiner* — Huy Q Phan
*Assistant Examiner* — Adam S Clarke
(74) *Attorney, Agent, or Firm* — Rossi, Kimms & McDowell LLP

(57) ABSTRACT

A monitoring method and system include an antenna disposed spaced from a structural member (SM), which itself can be the target object or attachable to a target object, without using any in-dwelling strain sensor. The antenna is arranged to not touch the SM in at least the no load condition. As the target object undergoes displacement and/or deformation, the SM undergoes displacement and/or deformation. The SM is juxtaposed, partially contained with, or fully contained within a magnetic or electromagnetic field and electromagnetically coupled to the emitting antenna. Characteristics of the electromagnetic field coupling between the antenna and the SM shift over time due to the displacement and/or deformation applied to the SM. The shift in the characteristics of the electromagnetic field coupling between the antenna and the SM over time can be used to determine the temporal change in deformation and/or
(Continued)

displacement of the SM over time to enable diagnosis of the target structural object being monitored.

26 Claims, 18 Drawing Sheets

Related U.S. Application Data

(60) Provisional application No. 62/571,554, filed on Oct. 12, 2017, provisional application No. 62/488,460, filed on Apr. 21, 2017.

(51) Int. Cl.
| | |
|---|---|
| *G01M 1/00* | (2006.01) |
| *G01N 3/06* | (2006.01) |
| *G01N 3/00* | (2006.01) |
| *G01N 3/20* | (2006.01) |
| *G01L 1/00* | (2006.01) |
| *G01L 1/14* | (2006.01) |
| *A61B 5/05* | (2006.01) |

(52) U.S. Cl.
CPC ............ *G01M 5/0041* (2013.01); *G01N 3/00* (2013.01); *G01N 3/066* (2013.01); *G01N 3/20* (2013.01); *A61B 5/05* (2013.01); *A61B 2562/0261* (2013.01)

(56) References Cited

U.S. PATENT DOCUMENTS

| | | | |
|---|---|---|---|
| 3,324,714 A | 6/1967 | Simon et al. | |
| 5,339,533 A | 8/1994 | Richardson | |
| 5,804,738 A | 9/1998 | Bach et al. | |
| 6,053,052 A | 4/2000 | Starostovic | |
| 7,581,446 B2 | 9/2009 | Troxler | |
| 8,971,024 B1 | 3/2015 | Tom et al. | |
| 9,326,728 B2 | 5/2016 | Demir et al. | |
| 2004/0139801 A1 | 7/2004 | Wilk | |
| 2006/0244580 A1 | 11/2006 | Nordmeyer | |
| 2007/0186677 A1 | 8/2007 | Zunino, III et al. | |
| 2010/0044574 A1 | 2/2010 | Nishino et al. | |
| 2010/0201378 A1 | 8/2010 | Costanzo et al. | |
| 2011/0152725 A1 | 6/2011 | Demir et al. | |
| 2012/0126833 A1* | 5/2012 | Dooley | G01N 3/066 324/657 |
| 2012/0154248 A1 | 6/2012 | Haque et al. | |
| 2014/0084909 A1* | 3/2014 | Pagani | G01N 33/383 324/209 |
| 2014/0182388 A1* | 7/2014 | Sipila | G01L 1/125 73/779 |
| 2016/0282504 A1* | 9/2016 | Wilson | E21B 47/0006 |
| 2019/0038214 A1* | 2/2019 | Mikhail | A61B 5/11 |

OTHER PUBLICATIONS

Written Opinion issued in Intl. Appln. No. PCT/US2018/028590 dated Jul. 5, 2018.
Muchaidze. "Installation and performance evaluation of coaxial cable sensors for crack and corrosion detection." Masters Theses. 2011: 95 pages.
International Search Report issued in Intl. Appln. No. PCT/US2019/025054 dated Jun. 10, 2019.
Written Opinion issued in Intl. Appln. No. PCT/US2019/025054 dated Jun. 10, 2019.
Rho et al. "Young's Modulus of Trabecular and Cortical Bone Material: Ultrasonic and Microtensile Measurements." Journal of Biomechanics. 1993: 111-119. vol. 26, No. 2.
Stein et al. "The Human Tibia A Simplified Method of Radiographic Analysis of its Cross-Section, With Anthropometric Correlations." Annals of Biomedical Engineering. 1979: 103-116. vol. 7.
Copending U.S. Appl. No. 16/460,249, filed Jul. 2, 2019 (a copy is not included because the cited application is not yet available to the public and the Examiner has ready access to the cited application).
Office Action issued in U.S. Appl. No. 16/460,249 dated Aug. 30, 2019.
Keysight Technologies. "Network Analyzer Basics." Training Manual. Jul. 31, 2014: 1-94. (Year: 2014).
Megson, T.H.G. "Structural and Stress Analysis" (2nd Edition) Ch 16. 2005: 467-547. Web. Aug. 27, 2019. Elsevier. <https://app.knovel.com/hotlink/toc/id:kpSSAE0005/structural-stress-analysis/structural-stress-analysis>.
Copending U.S. Appl. No. 16/589,736, filed Oct. 1, 2019 (a copy is not included because the cited application is not yet available to the public and the Examiner has ready access to the cited application).
Office Action issued in U.S. Appl. No. 16/460,249 dated Dec. 23, 2019.
Notice of Allowance issued in U.S. Appl. No. 16/460,249 dated Feb. 5, 2020.

* cited by examiner

FIG. 17

| | Mean Resonant Frequency/Load Slope Magnitude (Hz/N) | | | |
|---|---|---|---|---|
| | | Intact | 1C | 1.5C | 2C |
| | M7 Antenna 1 | 4.01 | 42.7 | 71.7 | 85.2 |
| | M7 Antenna 2 | 3.97 | 33.2 | 74.4 | 132 |
| | M8 Antenna 1 | 2.01 | 59 | 165 | 171 |
| | M8 Antenna 2 | 7.2 | 56.2 | 128 | 164 | p-values (t-test): Based on 3 tests for each specimen
$p < 0.05$

| | | 1C | 1.5C | 2C |
|---|---|---|---|---|
| M7 Antenna 1 | | | | |
| | Intact | 0.000732 | 0.000663 | 0.006714 |
| | 1C | | 0.028258 | 0.061433 |
| | 1.5C | | | 0.293666 |
| | | | | |
| M7 Antenna 2 | | 1C | 1.5C | 2C |
| | Intact | 3.74E-05 | 6.05E-07 | 7.83E-05 |
| | 1C | | 2.83E-05 | 0.000231 |
| | 1.5C | | | 0.001749 |
| | | | | |
| M8 Antenna 1 | | 1C | 1.5C | 2C |
| | Intact | 0.000191 | 2.63E-06 | 8.7E-06 |
| | 1C | | 6.04E-05 | 0.000103 |
| | 1.5C | | | 0.250535 |
| | | | | |
| M8 Antenna 2 | | 1C | 1.5C | 2C |
| | Intact | 6.86E-06 | 4.83E-07 | 3.16E-08 |
| | 1C | | 8.44E-06 | 6.29E-07 |
| | 1.5C | | | 9.59E-05 |

DISPLACEMENT AND DEFORMATION MONITORING METHOD AND SYSTEM WITHOUT USING ANY STRAIN SENSOR, AND COMPONENTS THEREOF

BACKGROUND

A strain sensing device can be attached to a structural member, such as an implant device subject to mechanical loading, to monitor the strain applied to the structural member. For example, U.S. Pat. No. 9,326,728 (hereafter Reference 1) discloses a wireless strain sensor having a resonating circuitry that is mounted to a structural member, including an implant device, and US 2007/0186677 discloses monitoring the strain applied to a target structural member, using one or more wireless strain sensors attached to the surface(s) of the target structural member, by monitoring the signals transmitted and/or reflected from the strain sensor using a known RF signal source.

Although using one or more strain sensors in the manner disclosed in Reference 1 can be beneficial in that the reflected resonance frequency can be set by designing the wireless sensor that is attached to the structural member, the strain sensors need to be imprinted, otherwise fabricated, or attached to the structural member to monitor the strain, increasing the cost and complexity of the system. It would be desirable to simplify the manner of monitoring deformation applied to a structural member by eliminating the in-dwelling strain sensor, which is in contact with the structural member. The present invention addresses this need.

SUMMARY

The present inventors have discovered that an in-dwelling strain sensor is not needed to monitor strain applied to a structural member.

One aspect of the present invention is a method of monitoring changes in a structural member (SM) as the SM undergoes at least one of displacement or deformation. The method can include a disposing step, an inducing step, an outputting step, a first determining step, and a storing step.

The disposing step disposes an antenna spaced from the SM so that the antenna does not contact the SM at least at no load condition. The inducing step induces a magnetic or electromagnetic field in the vicinity of the SM to create a coupling of the magnetic or electromagnetic field between the antenna and the SM, where characteristics of the magnetic or electromagnetic field coupling between the antenna and the SM are associated with one of the distance between the SM and the emitting antenna or the deformation state of the SM. The outputting step outputs electrical signals representing the characteristics of the magnetic or electromagnetic field coupling between the antenna and the SM, without using any strain sensing device directly attached to the SM. The first determining step determines the characteristics of the magnetic or electromagnetic field coupling between the antenna and the SM based on the electrical signals. The storing step stores the determined characteristics of the magnetic or electromagnetic field coupling between the antenna and the SM in a storage device.

The method can further include a repeating step of repeating the inducing step, the outputting step, the first determining step, and the storing step at a predetermined interval for one of an evaluation period or until a predetermined number of the characteristics of the magnetic or electromagnetic field coupling between the antenna and the SM has been determined.

The method can further include a second determining step of determining a shift in characteristics of the magnetic or electromagnetic field coupling between the antenna and the SM over the evaluation period or a time lapsed to determine the predetermined number of the characteristics of the magnetic or electromagnetic field coupling between the antenna and the SM.

The method can further include a third determining step of determining a temporal change in relative displacement or deformation of the SM over the evaluation period or the time lapsed based on the shift determined in the second determining step.

The method can further include a loading step of applying a known or measurable force or moment to the SM, an analyzing step of analyzing the determined characteristics in relation to the known or measurable force of moment applied to the SM in the loading step.

The inducing step can comprise using the antenna that has at least one wire configured to induce the magnetic or electromagnetic field and output the electrical signals, which is readable by a network analyzer, and the at least one wire is connectable to an input port of the network analyzer.

Alternatively, the inducing step can comprise using the antenna that has a first wire configured to induce the magnetic or electromagnetic field, and the outputting step can comprise using the antenna that further has a second wire configured to output the electrical signals, which is readable by the network analyzer. The first and second wires are connectable respectively to first and second input ports of the network analyzer.

Another aspect is a system for monitoring changes in the (SM) as the SM undergoes one of displacement or deformation. The system can include the antenna, an antenna holder, the network analyzer, and a controller.

The antenna can be configured to (a) induce, using a first electrical signal, a magnetic or electromagnetic field in the vicinity of the SM to create a coupling of the magnetic or electromagnetic field between the antenna and the SM, where characteristics of the magnetic or electromagnetic field coupling between the antenna and the SM are associated with one of the distance between the SM and the emitting antenna or the deformation state of the SM, and (b) output a second electrical signal representing the magnetic or electromagnetic field coupling between the antenna and the SM, without using any strain sensing device directly attached to the SM.

The antenna can comprise at least one wire configured to receive the first signal to induce the magnetic or electromagnetic field, and output the second signal, and the at least one wire is connectable to at least one input port of the network analyzer. Alternatively, the antenna can comprise a first wire configured to receive the first signal to induce the magnetic or electromagnetic field and a second wire configured to output the second electrical signal. The first and second wires can be connected respectively to first and second input ports of the network analyzer. The at least one wire and each of the first and second wires can comprise a coaxial cable.

The antenna holder can be configured to hold the antenna at a fixed distance from the SM so that the antenna is spaced from the SM and not contact the SM at least at no load condition.

The network analyzer can be configured to (a) output the first electrical signal to the antenna for inducing the magnetic or electromagnetic field, (b) receive the second electrical signal from the antenna, and (c) determine the characteristics of the magnetic or electromagnetic field coupling between the antenna and the SM based on the received second electrical signal.

The controller can include a memory storing instructions and a processor configured to implement instructions stored in the memory and execute a collecting task, a first determining task, and a second determining task. The collecting task can store, in the memory or another storage device, a plurality of characteristics of the magnetic or electromagnetic field coupling between the antenna and the SM determined at a predetermined interval by the network analyzer over an evaluation period. The first determining task can determine a shift in characteristics of the magnetic or electromagnetic field coupling between the antenna and the SM over the evaluation period. The second determining task can determine a temporal change in relative deformation or displacement of the SM over the evaluation period.

In an alternative embodiment, the system can include the antenna, the antenna holder, and the controller described above. Instead of the network analyzer, it can include a hardware interface configured to output the first electrical signal to the antenna and receive the second electrical signal and convert the received electrical signal to a third signal readable by the controller.

The processor of the controller is configured to execute a first determining task, a repeating task, a second determining task, and a third determining task. The first determining task receives the third electrical signal from the hardware interface and determines characteristics of the magnetic or electromagnetic field coupling between the antenna and the SM based on the third signal. The repeating task repeats the first determining task to obtain a plurality of characteristics of the magnetic or electromagnetic field coupling between the antenna and the SM determined by the first determining task at a predetermined interval over an evaluation period. The second determining task determines the shift in characteristics of the magnetic or electromagnetic field coupling between the antenna and the SM after each occurrence of the first determining task determining twice the characteristics of the magnetic or electromagnetic field coupling between the antenna and the SM at the predetermined interval, or collectively at the end of the evaluation period. The third determining task determines a temporal change in relative deformation or displacement of the SM over the evaluation period.

Another aspect is an apparatus for monitoring change in the SM as it undergoes one of deformation or displacement, using the antenna. The monitoring apparatus includes the controller and the hardware interface. The processor is configured to execute the first determining task, the repeating task, the second determining task, and the third determining task described above.

Another aspect is an antenna interface mountable to the SM, which is mountable to a target structural object, where the SM undergoes one of deformation or displacement. The antenna interface includes the antenna housing configured to be mountable to the SM and the antenna, where the output second electrical signal is usable to determine a temporal change in relative deformation or displacement of the SM over a predetermined evaluation period.

The SM can be mountable to a target object to be monitored, the SM undergoing the at least one of displacement or deformation as the target structural object undergoes at least one of displacement or deformation.

The change in relative displacement or deformation of the SM over the evaluation period or the lapsed time can be represented as a slope of resonant frequency/load. The degree of the slope can represent stability, with a higher slope representing a more unstable condition and a less slope representing a more stable condition.

BRIEF DESCRIPTION OF THE DRAWINGS

FIG. 17 illustrates the test results showing differences between the antenna of FIG. 4 and the antenna of FIG. 5.

DETAILED DESCRIPTION

Monitoring method and system, as well as components thereof, according to the present development can be used to determine a relative deformation on a structural member (hereafter SM for brevity), such as a beam, rod, or orthopedic hardware implanted in patients, without using any in-dwelling strain sensor.

Figure 1:
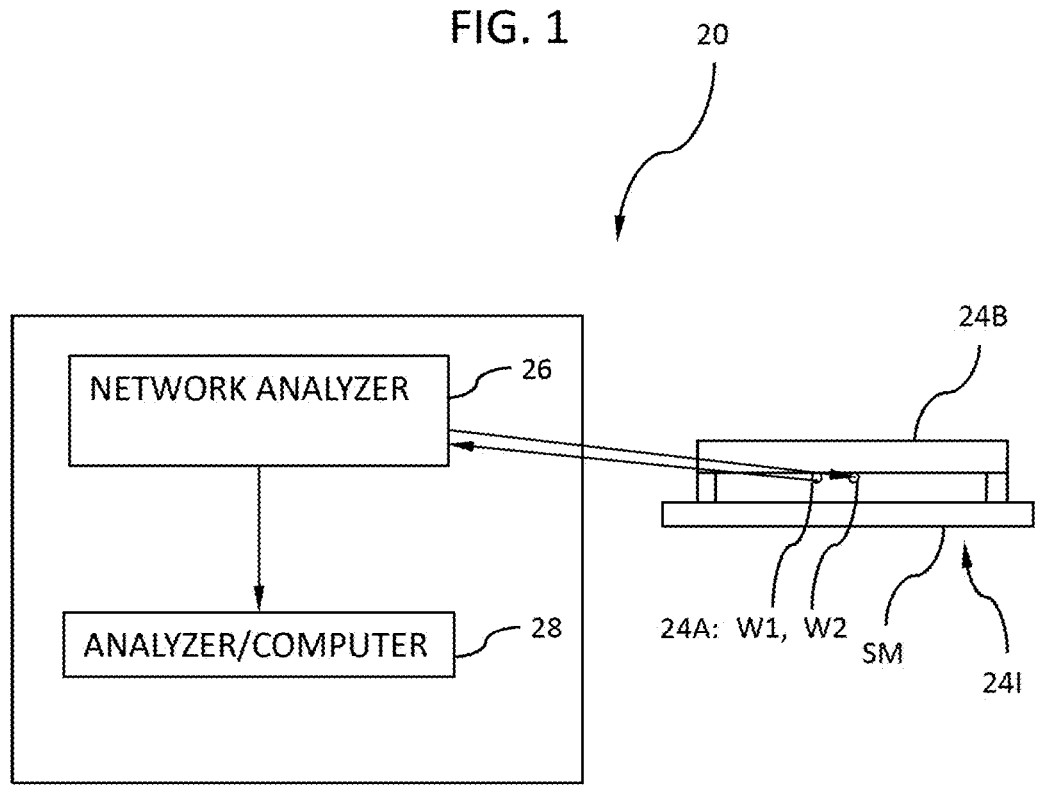
FIG. 1 schematically illustrates an embodiment of a present system for monitoring changes in a structural member.
Figure 2:
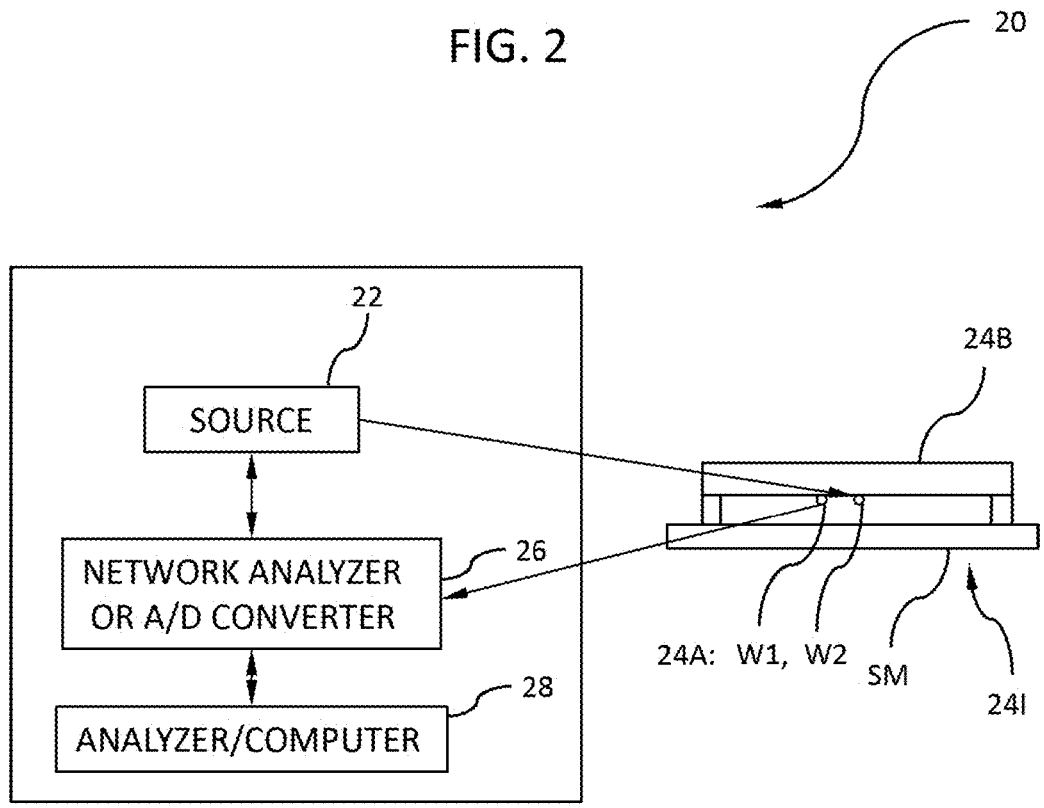
FIG. 2 schematically illustrates another embodiment of the present system for monitoring changes in the structural member.
Figure 3:
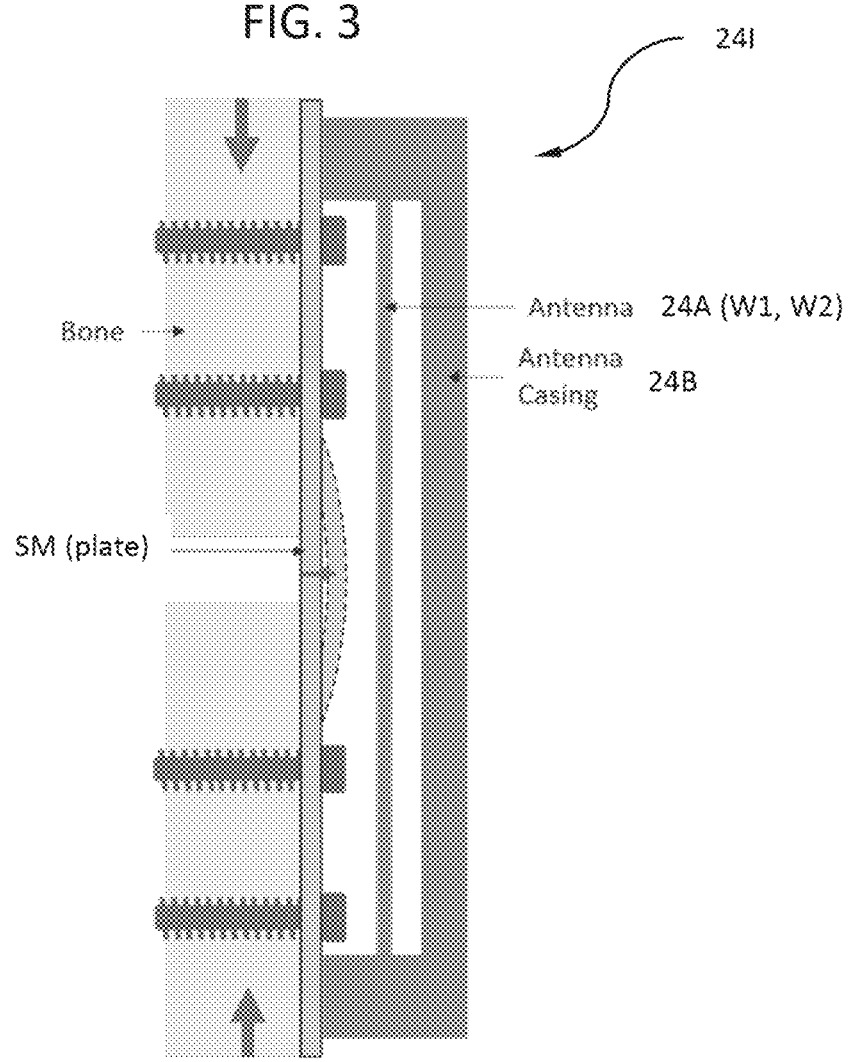
FIG. 3 schematically illustrates a sectional view of a present antenna interface that can detect the electromagnetic coupling between the structural member and the antenna.

Referring to FIGS. 1-3, the monitoring system 20, which includes an antenna interface 24I that includes an antenna 24A, can detect the displacement or deformation of the SM, such as a plate, relative to the antenna 24A, due to an applied load. An electromagnetic field is generated by a source, such as a network analyzer, and emitted using the antenna 24A over pre-determined frequency bandwidth sweeps. The antenna 24A receives signals from electromagnetic field, and alterations thereof. The pattern of the electromagnetic field changes with the SM's deformation state and/or distance between the SM and the antenna 24A, with shifts in the characteristics of the electromagnetic field coupling between the antenna and the SM being representative of the SM's deformation and/or distance change between the SM and the antenna 24A. The characteristics of the electromagnetic field coupling between the antenna and the SM are determined by analysis of the electrical signals from the antenna 24A. These electrical signals can be analyzed to determine the properties of the antenna and include, but are not limited to, the resonant frequency, response magnitude of the S parameters, and impedance. The electromagnetic field data are analyzed to determine characteristics of the electromagnetic field coupling between the antenna and the SM over an evaluation period. Accordingly, the temporal changes in the relative deformation of the SM can be monitored based on the shift in characteristics of the electromagnetic field coupling between the antenna and the SM over the evaluation period.

Referring to FIG. 3, the antenna interface 24I measures the load on a fixation plate SM used to stabilize a fractured bone. The compressive load on the bone causes the plate SM to bend, and the resulting displacement of the plate SM relative to the antenna 24A is detected as a shift in the antenna's resonant frequency. Specifically, the antenna interface 24I houses the antenna 24A, which can be composed of a pair of wires (or poles) W1, W2 providing a Port 1 and Port 2 configuration of a dipole antenna, or a single pole antenna using just a single wire W1 or W2. At least one bare wire portion is disposed in the vicinity of the SM so that the SM is juxtaposed to, partially within, or entirely within the electromagnetic field emitted by the antenna. The antenna interface 24I includes an antenna housing 24B composed of a non-conductive material(s) to hold the antenna 24A in a fixed reference position. The antenna housing 24B can function as a spacer that maintains the bare antenna wire portion(s) spaced from and substantially parallel to the SM so that the bare wire portions are at a fixed distance from a reference point or points on the SM, while not coming in contact with the confronting surface of the SM at the no load condition and at expected higher load condition (e.g., 500N). Alternatively, the antenna housing 24B can be fixed to a structure other than the target SM to hold the antenna 24A in a fixed reference position but not in contact with the SM. Since the antenna is disposed spaced from the SM so that it does not come in contact during use, the present system is wireless.

Figure 4:
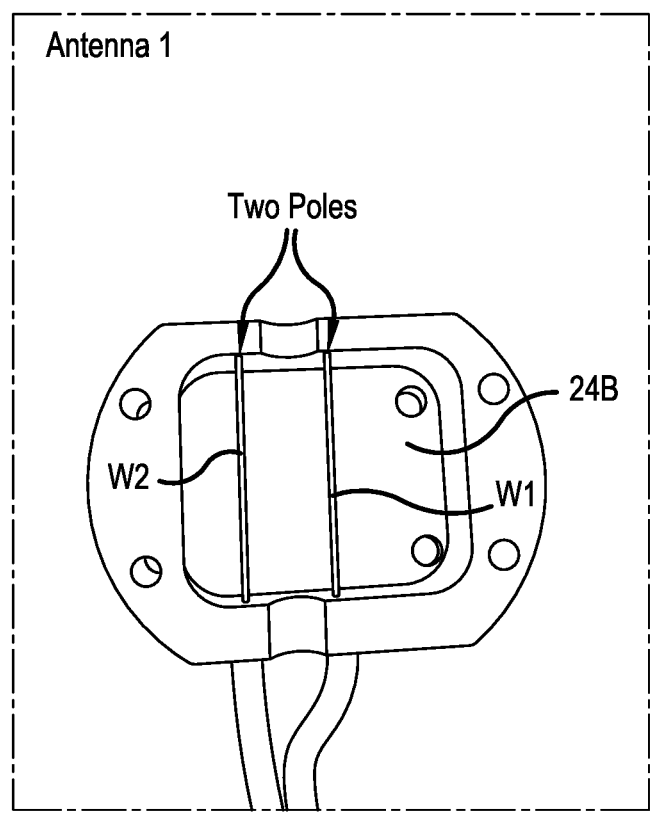
FIG. 4 illustrates a first embodiment of an antenna that can be used in the systems of FIGS. 1-2.

The antenna illustrated in FIG. 4 uses a dipole configuration with a pair of poles (wires W1, W2) of the antenna 24A that can be connected to port 1 and port 2 of the network analyzer 26 in the system of FIG. 1. The SM is located between the two poles (wires W1, W2). The network analyzer 26 and the antenna 24A function as a transceiver that outputs and inputs electrical signals. The pair of poles can be disposed parallel to each other. Each pole can be a coaxial cable. The shielding of the coaxial cables is removed to expose the inner wire at the end of the coaxial cables. One of the two wires can be used as a probe and the other to receive signals corresponding to the characteristics of the electromagnetic coupling. Specifically, an interrogating electromagnetic field can emanate from one (e.g., W1) of the two wires W1, W2, while the other wire (e.g., W2) receives the characteristics of the electromagnetic field coupling between the antenna and the SM so that the electromagnetic field coupling can be monitored. The antenna outputs the characteristics of the electromagnetic field coupling between the antenna and the SM as electrical signals. For example, the network analyzer obtains or calculates the S12 parameter, which can represent the ratio of power transferred from port 2 to port 1. At the antenna's resonant frequency, the power transfer is most efficient, and the S12 response, which is typically measured on a decibel scale, reaches a local maxima.

Figure 5:
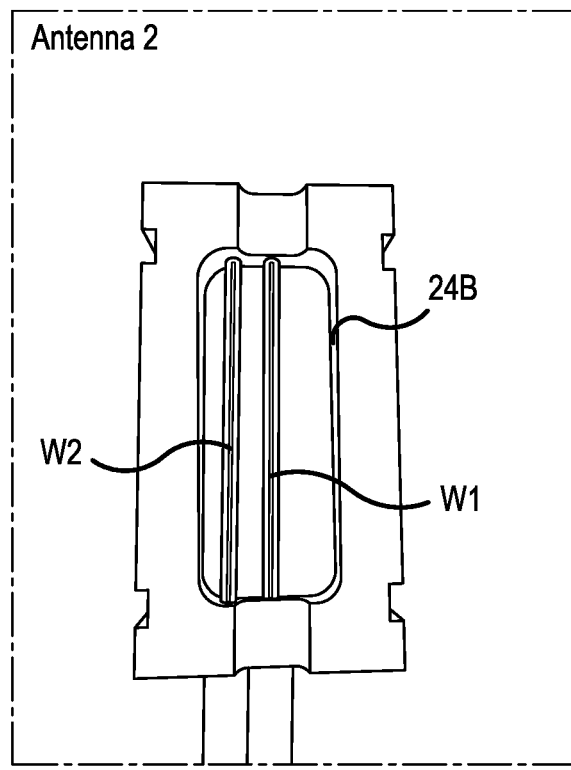
FIG. 5 illustrates a second embodiment of the antenna that can be used in the systems of FIGS. 1-2.

A second antenna variant, illustrated in FIG. 5, also uses a dipole configuration. But for this antenna variant, only the S11 parameter is obtained. The S11 parameter is measured with port 1 wire W1 centered in front of the SM. Rotations of the antenna have smaller effect on the location of antenna relative to the SM to improve consistency. Specifically, the S11 parameter represents the ratio of the power sourced at port 1 that is returned back to port 1, also known as the "return loss." At the antenna's resonant frequency, the S11 parameter reaches a local minima. The second pole (wire W2) of the antenna can be connected to port 2 of the network analyzer to ground the shielding, or the shielding of the second pole (wire W2) can be grounded directly to the shielding of the first cable. But the second pole (wire W2) can be a dud as, while the shieldings of both wires are grounded, the second pole (wire W2), which is an offset pole, is not connected to anything. Although the second pole (wire W2) is not directly used in signal analysis, it helps to eliminate noise compared to a monopole antenna. For either antenna configuration, the SM affects the frequency at which the local maxima or minima occurs.

Figure 6:
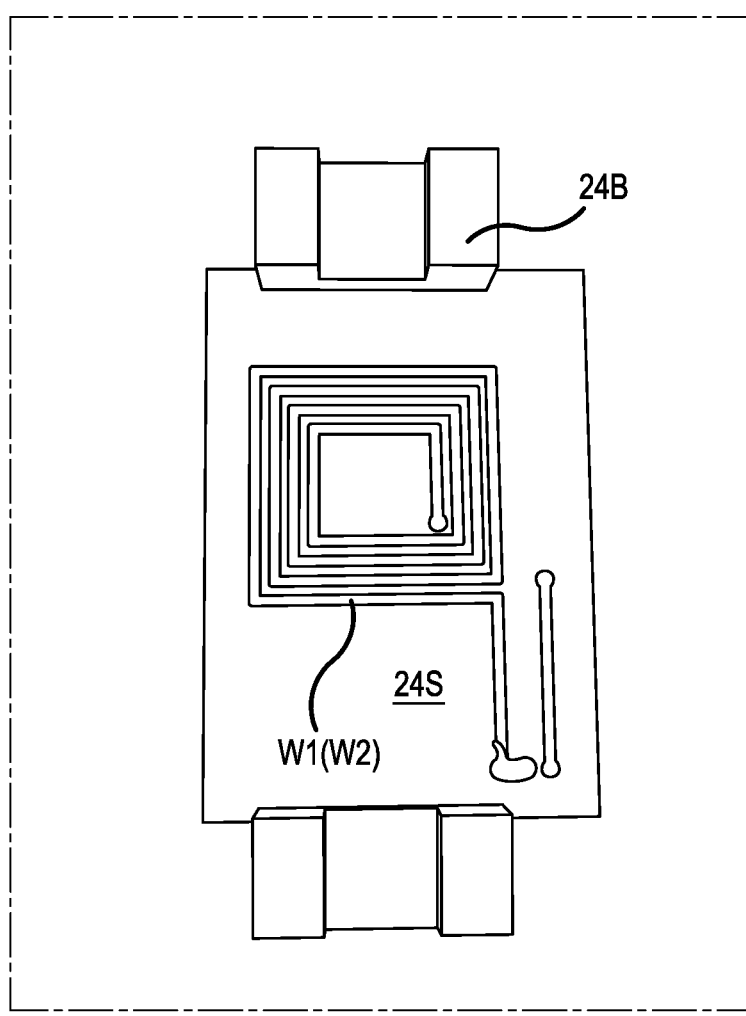
FIG. 6 illustrates a third embodiment the antenna that can be used in the systems of FIGS. 1-2.

A third antenna variant, illustrated in FIG. 6, has a coiled or loop configuration, where the antenna 24A comprises a coiled wire W1, W2 is disposed on each side of a substrate 24S, which can be made of a dielectric material. The two coil wires W1, W2 are symmetrical and are disposed aligned with each other, with the substrate being sandwiched between them, providing a spacing therebetween in the thickness direction of the substrate. Each of the two coil wires terminates inside the coil. The two terminating ends of the two coil wires disposed at the farthest interior points of the coils are electrically connected through the dielectric material, while the two ends terminate outside of the coils. Accordingly, the antenna functionally is a single conductor. One outer end of the coils connects to an inner wire of a coaxial cable, while the other outer end of the coils connects to the shielding of the coaxial cable.

In the embodiment of FIG. 6, the illustrated side of the coil wire W1 would be disposed on the side facing the SM. This embodiment uses only one coaxial cable connected to the network analyzer to obtain the S11 parameter. That is, the antenna connects, via the coaxial cable, to a single port of the network analyzer, which obtains the S11 parameter. The resonant frequency is found at the local minima of the S11 parameter. The antenna illustrated in FIG. 6 can have a resonant frequency of 200 MHz.

Figure 7:
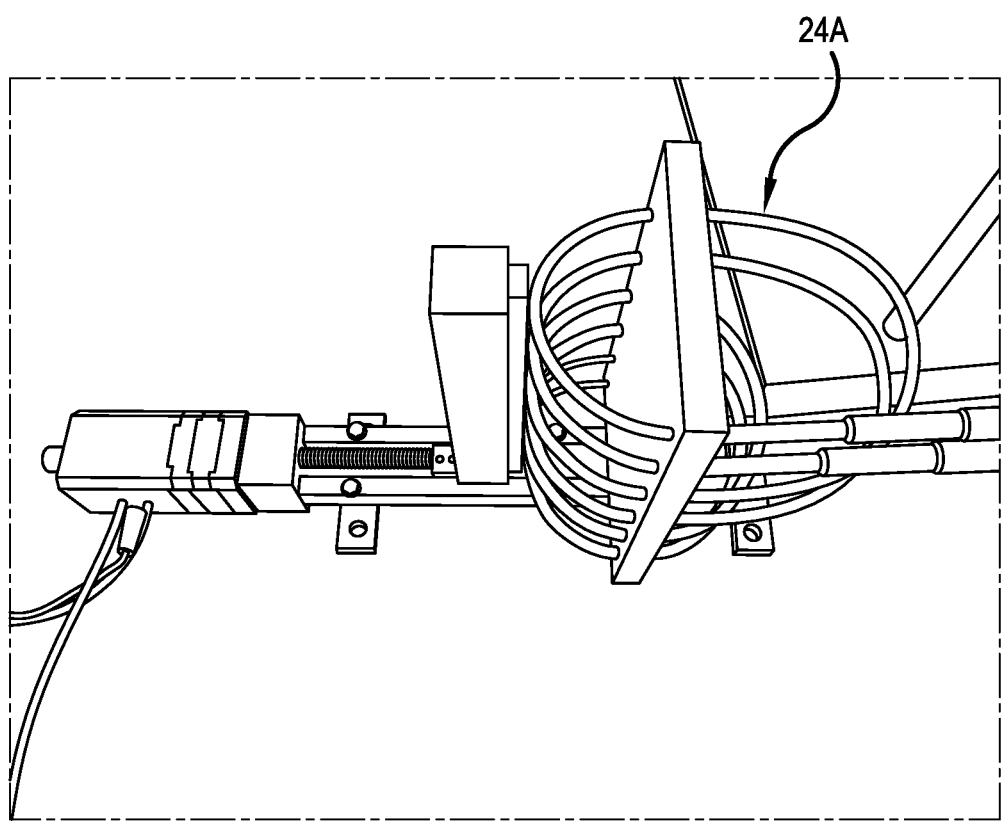
FIG. 7 illustrates a fourth embodiment the antenna that can be used in the systems of FIGS. 1-2.

A fourth antenna variant, illustrated in FIG. 7, uses a similar dipole configuration as the antenna of FIG. 5, with only one (e.g., W1) of the two coaxial cables connected to the network analyzer to obtain the S11 parameter. This antenna 24A, however, is coiled and the SM is interrogated from the side of the coiled (unexposed) cables instead of being interrogated at the tip where the inner wire is exposed. The signal strength is greater in this configuration because there are specific locations along the length of the wire where the shift in signal is greatest. These locations depend on the resonant frequency harmonic that is measured. The coiled shape further increases the signal strength by aligning 3 locations along the wire length where the signal is strongest. For this configuration, the antenna parameters can be optimized by adjusting the antenna length, spacing between cables, and resonant frequency harmonic while interrogating a stainless steel bar at known distances from the antenna. The resulting signal strength and noise were calculated. In brief, increasing the spacing between wires increases the signal strength but also increases the noise. Higher frequency harmonics also result in a stronger signal but greater noise.

Upon directing and emitting an alternating magnetic or electromagnetic field through a pre-determined frequency sweep using a source 22 toward the SM, the SM interacts with the applied electromagnetic field through near field effects. The source 22, in one embodiment, can be an inductor that produces an alternating electromagnetic field. The SM is electromagnetically coupled to the antenna 24A. The distance between the SM and the antenna 24A can be represented by characteristics of the electromagnetic field coupling between the antenna and the SM. As the distance between the antenna 24A and the SM changes then the characteristics of the electromagnetic field coupling between the antenna and the SM become shifted because the fundamental coupling between the antenna 24A and the SM is altered. For example, one way of inducing deformation in the SM, and thus affect a change in distance between the antenna 24A and the SM, is to apply a mechanical load to the SM while the antenna 24A remains fixed in space, resulting in an alteration in the resonance frequency due to changes in the electromagnetic coupling between the antenna 24A and the SM. The S-parameters of the antenna can be obtained by the connected network analyzer 26 or the connected analyzer/computer 28 if an A/D converter is used to interface the antenna 24A thereto. The analyzer/computer 28 can determine the resonance frequency, as well as the S-parameter magnitude of the antenna 24A if coupled to the SM via the A/D converter, without the need for any strain sensor directly attached to the SM. The antenna 24A is spaced from the SM so that it does not touch any surface of the SM during the operational conditions.

The electromagnetic field surrounding the antenna is affected by objects in the near field range due to the conductive and/or dielectric properties of the object. A conductive material has an eddy current induced, which in turn causes the material to act as an antenna itself, thus altering the electromagnetic field. A non-conductive dielectric material can also alter the electromagnetic field via the electromagnetic polarization of the material. Therefore, the SM can be any material that is conductive and/or has a relative permittivity (i.e., dielectric constant) that is different than the relative permittivity of the surrounding medium (e.g. air).

In the embodiment of FIG. 1, the components of the present monitoring system 20 includes a network analyzer 26, such as a commercially-available Tektronix TTR503A Network Analyzer and Rohde & Schwarz ZVB4, which can apply electromagnetic fields in the radio frequency spectrum, the antenna interface 24I, which includes the antenna 24A, including any wire extension extending from the antenna wires W1, W2, the antenna housing 24B, and an analyzer 28, which can be a computer that reads and analyzes the data output from the network analyzer or stored over a period, or otherwise receives data that has been accumulated over the period. The operating frequency range of the present monitoring system can be 10 MHz to 4 GHz, with the preferred range being 40 MHz to 500 MHz for biomedical applications.

The embodiment of FIG. 2 is similar to the embodiment of FIG. 1, except that it includes a separate source 22, which can be an inductor or other conventional apparatuses for applying electromagnetic fields in the radio frequency spectrum. In this instance, the network analyzer can be an A/D converter, and the analyzer/computer 28 can execute the functions of the network analyzer 26 using software.

Figure 8:
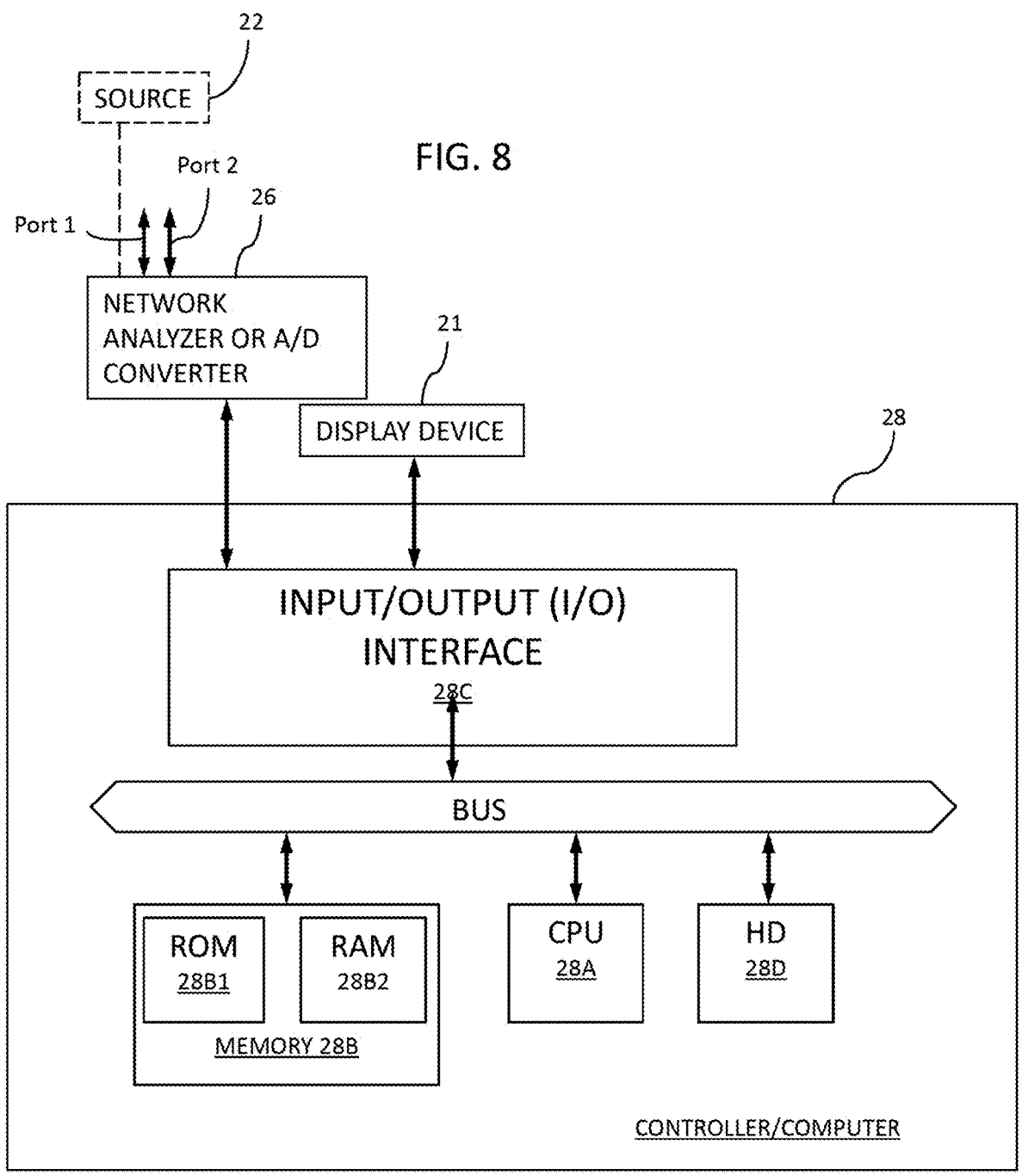
FIG. 8 illustrates a controller or computer that determines the instantaneous or temporal change in the structural member over a period of time.

FIG. 8 schematically illustrates the analyzer, which comprises a controller or computer that can be programmed to analyze the shifts in the characteristics of the electromagnetic field coupling between the antenna and the SM over an evaluation period or a predetermined number of measurements of the characteristics of the electromagnetic field coupling between the antenna and the SM obtained over a predetermined interval. The computer includes CPU (processor) 28A, memory 2(B), I/O (input/output) interface 28C. The I/O interface 28C can include a communication interface, such as Ethernet, for communication to a network and Internet, a display interface 21, and typical interfaces, such as USB, for connecting peripheral devices, including a keyboard and a mouse, as well as the network analyzer or any other device that can obtain the frequency sweep from the electrical signals obtained from the antenna 24A. The network analyzer 26 can be either a standalone apparatus, which can also be connected to the computer via the I/O interface 28C, or a peripheral device that converts the electrical signals from the antenna 24A into digital signals (e.g., A/D converter) readable by the computer, and can be connected to the computer 28 via either the Ethernet, USB or serial port.

The computer 28 can determine the characteristics of the electromagnetic field coupling between the antenna and the SM from the electrical signal data obtained by the network analyzer 26 across a pre-determined frequency range. The functions of the network analyzer are well known and are commercially available either as a standalone unit or software operated unit using an A/D converter, such as a commercially available Tektronix TTR503A and Rohde & Schwarz ZVB4 network analyzers. Alternatively, the computer 28 can analyze the stored data of the characteristics of the electromagnetic field coupling between the antenna and the SM determined and read over an evaluation period or a predetermined number of times read over a predetermined interval by the network analyzer 26. The storage device can be a memory drive within the computer itself, flash memory, network drive, or remote database connected over the Internet.

The memory 28B communicates with the CPU 28A via a bus. The memory 151 can include a ROM 28B1 and a RAM 128B2. The memory 28B also can be configured as a non-volatile computer storage medium, such as a flash memory, instead of the RAM and the ROM. The computer 28 can also include a removable memory (e.g., flash card) connected via the I/O interface using, for example, USB or any other conventional memory card interface, and conventional hard disk 28D. The memory 28B and hard disk 28D are some embodiments of a non-transitory machine-readable medium that can store instructions, which, when executed by the processor, that perform various operations. These operations include, but are not limited to, controlling/operating the source 22 connected to the I/O interface 28C, controlling/operating the network analyzer connected to the I/O interface 28C, determining the characteristics of the electromagnetic field coupling between the antenna and the SM, determining the shift in characteristics of the electromagnetic field coupling between the antenna and the SM based on the electrical signals received from the antenna 24A in response to an electromagnetic field applied at different times over an evaluation period, and determining the temporal change in deformation and/or displacement of the SM, based on the shift in characteristics of the electromagnetic field coupling between the antenna and the SM.

Figure 9:
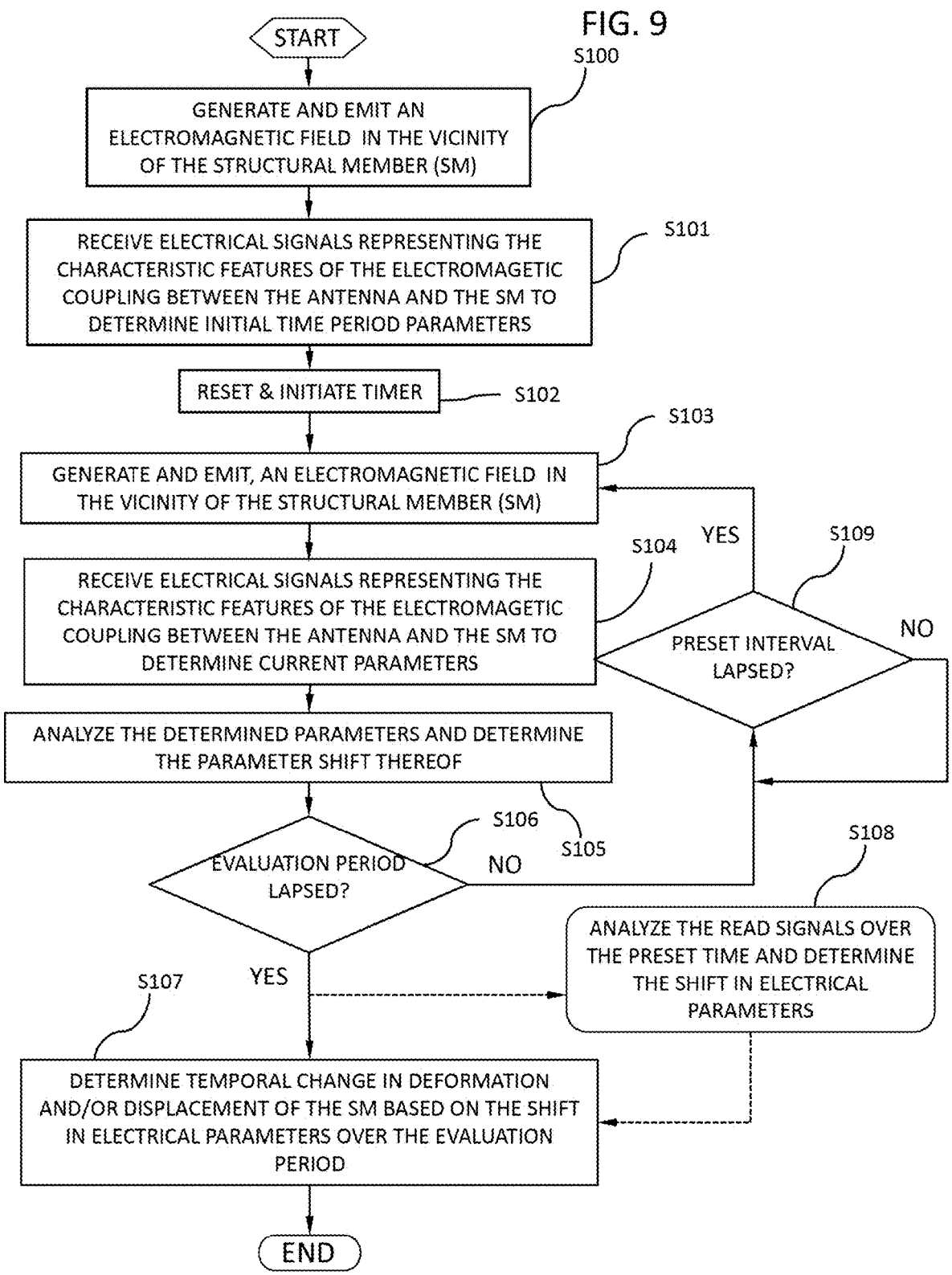
FIG. 9 illustrates an operational diagram, namely a flowchart of the present system for monitoring changes in the structural member.

FIG. 9 illustrates an operational flow of the present monitoring system that can monitor the changes in the SM. After the SM has been mounted to the target area to be monitored, at S100, the source 22 or network analyzer 26 is controlled to generate, emit, or direct an electromagnetic field over a pre-defined frequency bandwidth towards the SM. The SM interacts with the emitted electromagnetic field when it is subject to an alternating magnetic or electromagnetic field. In S101, the antenna 24A outputs electrical signals based on the coupled electromagnetic field. The electrical signals from the antenna 24A are input to the network analyzer 26 (or A/D converter) that reads the received electrical signals. After determining the initial characteristics of the electromagnetic field coupling between the antenna and the SM, which represents these parameters at the initial time period, they can be stored in the analyzer/computer 28 and/or stored to a database or a portable storage device.

At S102, after determining the initial characteristics of the electromagnetic field coupling between the antenna and the SM, a timer or a counter is reset (i.e., starting point at which the initial characteristics of the electromagnetic field coupling between the antenna and the SM were determined). This can be done using a computer or a standalone timer. Alternatively, the technician monitoring the target area can keep a calendar or manually keep track of the time and date as to when the characteristics of the electromagnetic field coupling between the antenna and the SM were read. At a predesigned time interval after the initial characteristics of the electromagnetic field coupling between the antenna and the SM have been determined, process/step S103 essentially repeats process/step S100, and process/step S104 repeats process/step S101 to determine the current characteristics of the electromagnetic field coupling between the antenna and the SM.

At S105, the analyzer or computer 28 can analyze the previously determined characteristics of the electromagnetic field coupling between the antenna and the SM and the currently determined characteristics of the electromagnetic field coupling between the antenna and the SM and determine the shift of the characteristics of the electromagnetic field coupling between the antenna and the SM by comparing the determined characteristics of the electromagnetic field coupling between the antenna and the SM over different times. Alternatively, the shift in the characteristics of the electromagnetic field coupling between the antenna and the SM can be determined after determining a predetermined number of characteristics of the electromagnetic field coupling between the antenna and the SM over a desired evaluation period, or after the desired evaluation period has lapsed (where a desired total number of characteristics of the electromagnetic field coupling between the antenna and the SM for the desired evaluation period has been determined) (see S107).

At S106 the analyzer 28 determines whether the evaluation period or the desired total number of characteristics of the electromagnetic field coupling between the antenna and the SM has lapsed after determining each of the characteristics of the electromagnetic field coupling between the antenna and the SM other than the determination of the initial characteristics of the electromagnetic field coupling between the antenna and the SM. If the negative (NO in S106), after the preset interval has lapsed (YES) at S109, processes/steps S103-S105 are repeated until affirmative in S106 (YES). If affirmative (YES in S106), at S107, the analyzer 28 determines the temporal change in deformation and/or displacement of the SM based on the shift in the characteristics of the electromagnetic field coupling between the antenna and the SM over the evaluation period. The temporal changes in relative deformation and/or displacement of the SM are determined based on the determined shift over the evaluation period. The actual temporal changes in deformation and/or displacement of the SM can be determined by implementing an a priori deformation-electrical parameter or displacement-electrical parameter calibration of the hardware. Data from an electrical parameter-deformation or electrical parameter-displacement calibration, performed in advance, can be stored in memory 28B accessible by the analyzer 28.

For example, the electrical parameter signal, such as resonant frequency, can be calibrated to determine the strain on the surface of the SM. This can be done by first applying a known load and measuring the strain on the SM with a conventional wired strain gauge to determine the relationship between strain and load. The resonant frequency measurement can then be made while applying an identical load to the SM to determine the relationship between load and resonant frequency. Because the relationship is known between the resonant frequency and the load, and between the load and the strain on the SM, the relationship can be determined between the resonant frequency and the strain. The resonant frequency measurement can therefore be calibrated to give a direct measure of strain for that particular SM, environment, and antenna setup.

The shift in characteristics of the electromagnetic field coupling between the antenna and the SM can be used rather than the absolute values of the determined characteristics of the electromagnetic field coupling between the antenna and the SM in determining the temporal relative changes in displacement and/or deformation of the SM. Based on the temporal changes in relative displacement and/or displacement of the SM, changes in the target area or biological subject can be determined. For instance, for a fracture fixation plate implanted in a person, these changes can be monitored for use in the diagnosis and the prognosis for the healing of the bone fractured in the person. For a spinal fixation device, these changes can be used to determine the course of fusion progression.

The present development is particularly useful for monitoring relative load sharing when the SM is an orthopedic implant, where the displacement and/or deformations are typically small. This allows for monitoring the load applied to a fixation plate for stabilizing a bone fracture. Referring to FIG. 2, which illustrates a SM composed of a fixation plate attached to a bone, when the plate-bone construct is loaded in compression, the fixation plate bends along with the bone, displacing the fixation plate. The electronic signals in the antenna 24A, which is disposed fixedly spaced from the SM (at least in the non-load condition), are affected by the electromagnetic coupling between the antenna 24A and the SM, which relates to characteristics of the electromagnetic field coupling between the antenna and the SM that vary according to the relative distance between the fixation plate and the antenna 24A. These characteristics of the electromagnetic field coupling between the antenna and the SM are a function of this distance, which is, in turn, a function of the applied load carried by the SM. Therefore, these characteristics of the electromagnetic field coupling between the antenna and the SM can be calibrated based on the known load conditions to determine the load borne by the SM.

In the case of a fixation plate stabilizing a bone fracture where there exists a distinct gap between the fracture bone termini, where the plate is the SM of interest, it is known that the majority of the load applied to the plate-bone construct is initially carried by the plate. With this known initial loading condition, the characteristics of the electromagnetic field coupling between the antenna and the SM can be calibrated to determine the load carried by the SM relative to the load applied to the plate-bone construct throughout the temporal healing of the bone. Subsequent measurements of the relative load carried by the SM therefore require the application of a known load to the plate-bone construct.

When applying the present methodology to fracture healing, the objective is to determine the level of healing that has occurred by testing the mechanical stability of the bone-implant construct. As the healing progresses, the stability increases. As the stability increases, the relative load borne by the implant decreases, and the signal from the antenna, such as resonant frequency shift, also decreases because it is a measure of the load on the implant. See FIGS. 14, 17, and 18. Calculating the shift in resonant frequency relative to the load applied to the bone-implant construct provides a measure of the relative load borne by the implant. Therefore, the slope of the resonant frequency versus applied load curve is calculated. This slope is a good indicator of the stability and level of healing of the bone. By determining this slope over time and comparing it to an initial measurement, one can determine how the fracture is healing over that time frame.

This methodology is particularly useful for monitoring the relative load on the plate at predetermined time points, such as every two weeks, throughout the healing of the fracture in order to monitor or predict the healing progress. As a fracture heals, the new tissue that grows progressively stabilizes the fracture, and therefore increases the relative load borne by the bone and decreases the relative load borne by the orthopedic plate. As the load on the plate decreases, the deformation of the plate decreases proportionally, and the characteristics change accordingly. Calculating the shift in the signal, such as resonant frequency, relative to the load applied to the plate-bone construct provides a measure of the relative load on the plate. Therefore, the signal from the antenna is plotted against the load applied to the construct, and the slope of the resulting curve can represent the stability of the construct and the level of healing. If the fracture is not healing properly, the load on the plate changes slowly or does not change over time. By taking temporal measurements, a physician can monitor healing progress by determining the change in load on the plate relative to the initial measurement. The measurement can therefore provide the physician with an early indicator if the fracture is not healing normally and may need further treatment.

Figure 10:
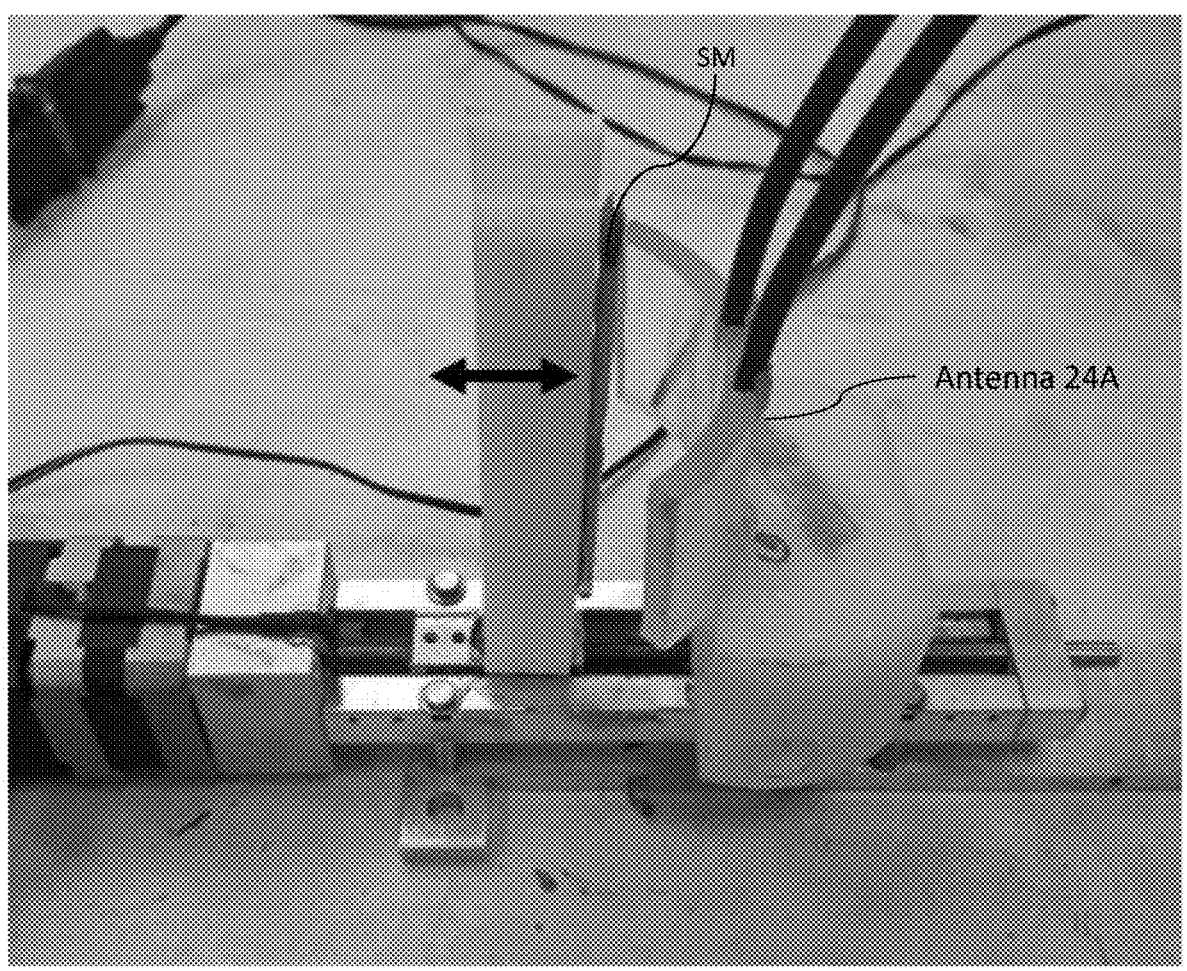
FIG. 10 illustrates a testing setup for measuring the effects of plate (SM) displacement relative to the antenna.

FIG. 10 illustrates a testing setup to measure the effects of a metal plate SM displacement relative to the antenna, namely to demonstrate a benchtop experiment where the metal plate SM is attached to a polymeric block with screws. The plate-block construct is rigidly affixed to a linear actuator. A two prong antenna 24A is kinematically constrained to the linear actuator base and remains fixed in space during the entire experiment. The plate-block construct is slowly displaced away from the antenna 24A at a known rate so that the distance between the antennae 24A and the SM is known at all times during the experiment. An electromagnetic field is continually emitted by one pole of the two pole antenna 24A towards the SM over a predetermined frequency bandwidth (for example, for the experiment depicted in FIG. 10, the frequency bandwidth was swept from 85 MHz to 90 MHz), and the electromagnetic field coupling between the SM and the antenna is continually recorded by the second pole of the antenna 24A.

Figure 11A:
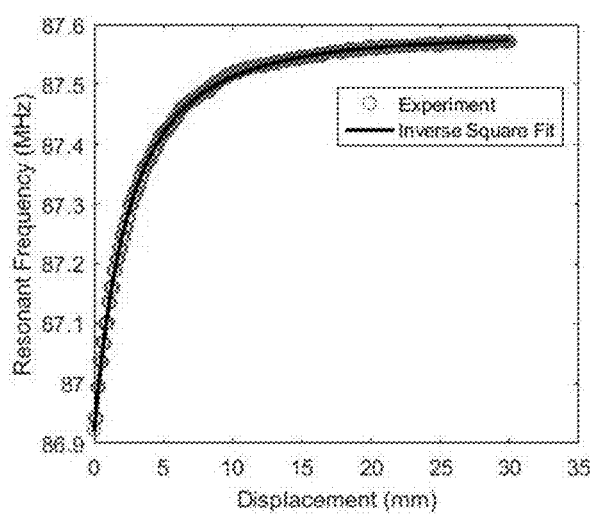
FIGS. 11A and 11B illustrate plots of resonant frequency versus displacement of a metal plate (SM), showing that the displacement of the metal plate relative to the antenna shifts the system's resonant frequency, FIG. 11A showing that the frequency shift follows an inverse square relationship, while FIG. 11B showing that the curve can be well approximated with a linear model when focused on a short displacement range.
Figure 11B:
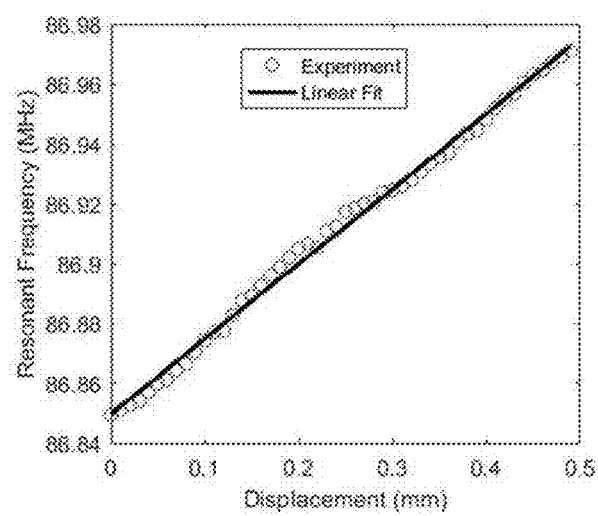

The displacement of the plate SM relative to the antenna causes a shift in the antenna's resonant frequency measure by the S-parameter. FIG. 11A demonstrates the non-linear (inverse square fit) resonance frequency dependency on the distance between the plate-block construct and the antennae 24A. That is, the frequency shift follows an inverse square relationship. FIG. 11B demonstrates the highly linear relationship resonance frequency dependency at very small distances (labeled displacements for this experiment) between the plate-block construct and the antenna 24A. That is, when focused on a short displacement range, the curve can be approximated with a linear model.

Figure 12:
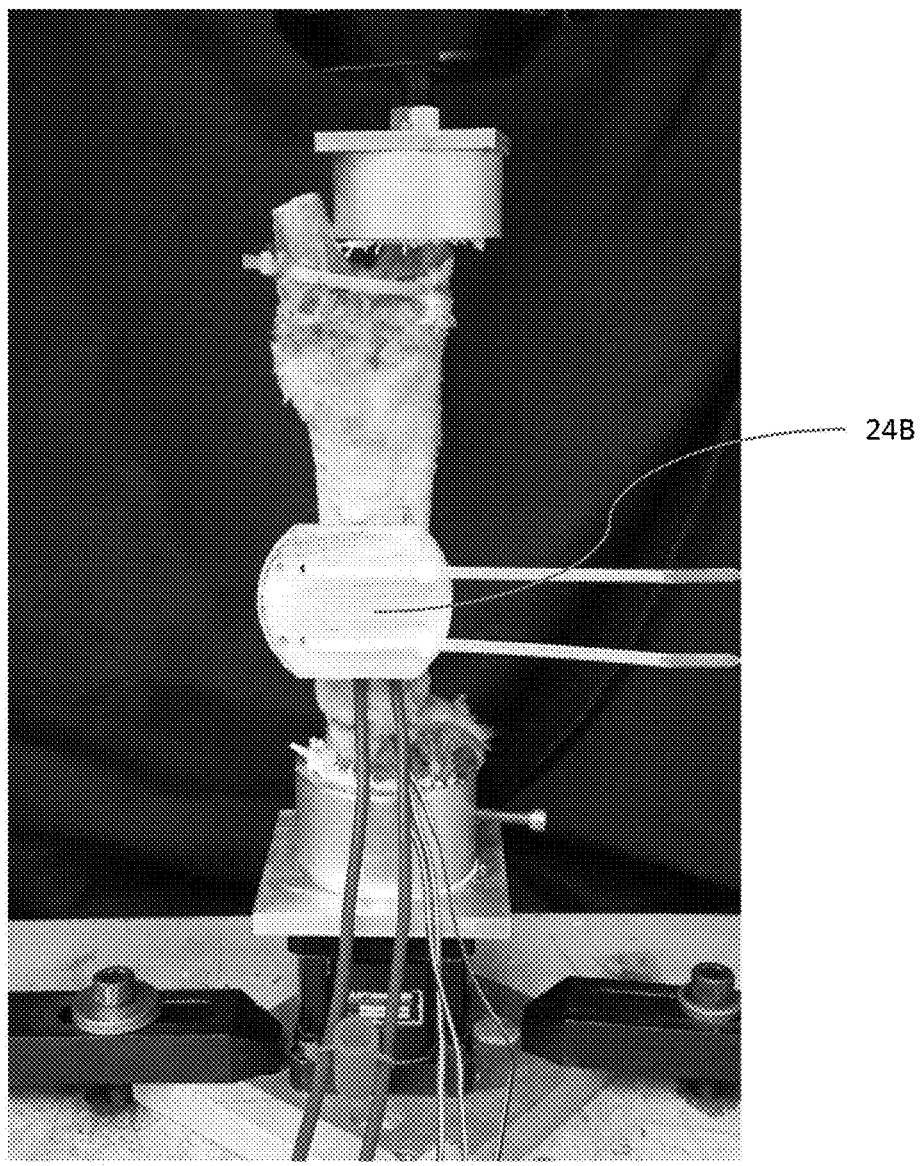
FIG. 12 illustrates another testing setup for a sheep metatarsal bone, where a metal plate has been mounted with a strain gauge attached to the plate, and the antenna according to the present invention clamped to the structure.
Figure 13:
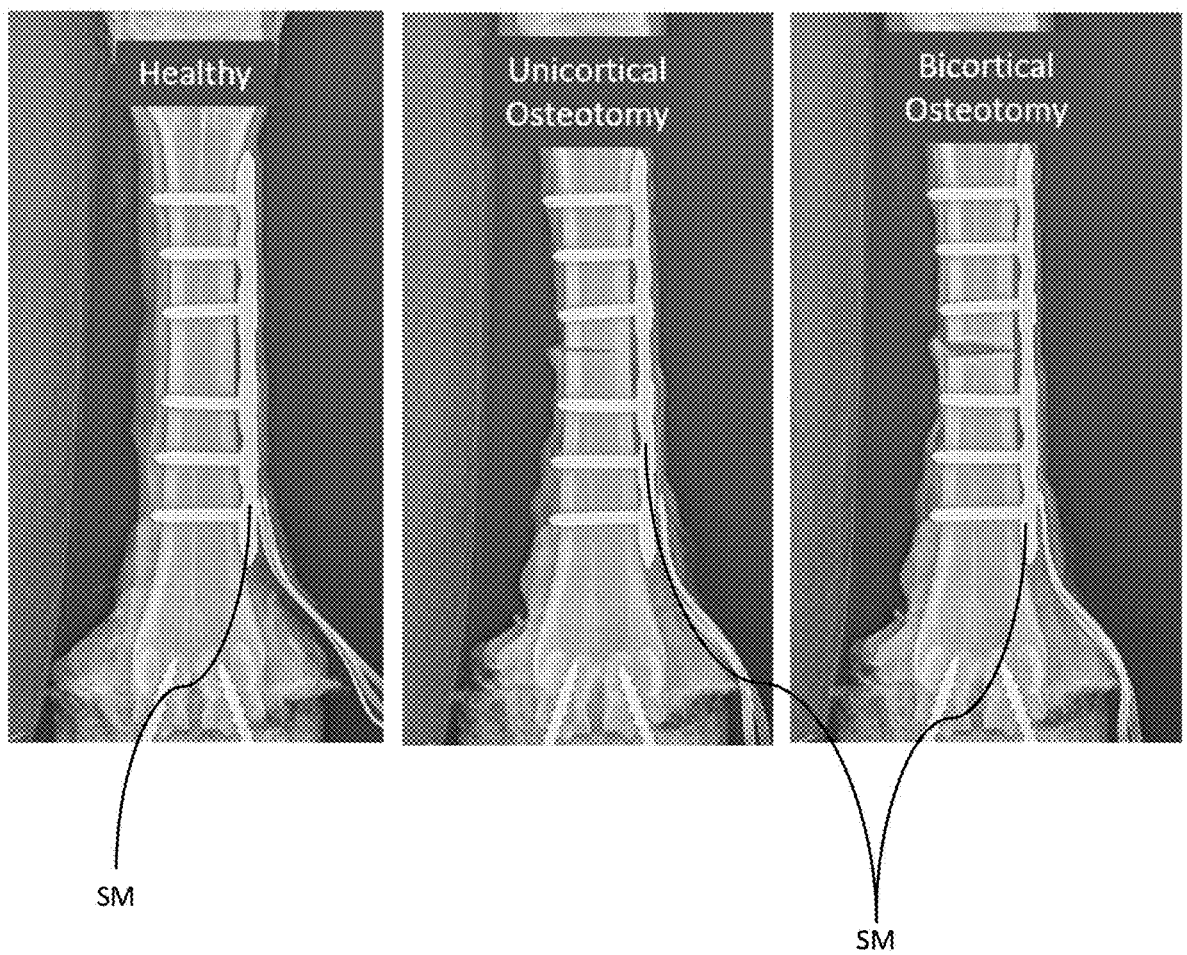
FIG. 13 illustrates radiographs of three different metatarsal bone conditions for testing in the setup of FIG. 12.

FIG. 12 shows a benchtop experimental setup used in testing a sheep metatarsal bone with a strain gauge attached to the fixation plate SM and antenna clamped thereto. The center of the fixation plate was instrumented with a conventional strain gauge rosette in order to directly measure the strain imparted on the plate. The antenna illustrated in FIG. 3 was clamped to the plate-bone construct, which was then loaded in compression from 0 to 500 N. The same plate-bone construct was tested in three bone conditions to simulate a fracture and the increased stabilization of the bone as a fracture heals. As shown in FIG. 10, these three conditions were healthy (intact), unicortical osteotomy (partially destabilized bone), and bicortical osteotomy (full fracture).

Figure 14:
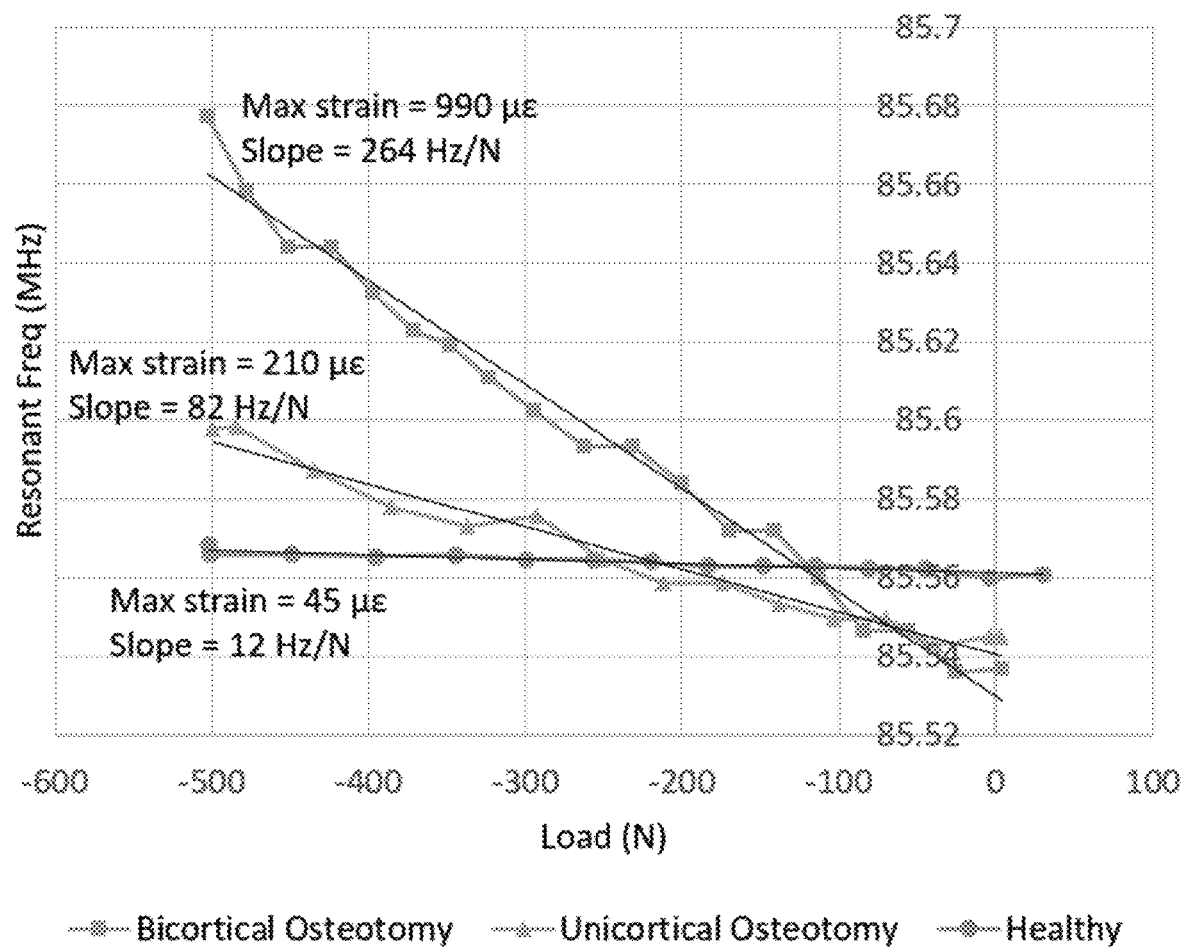
FIG. 14 illustrates a plot of the resonant frequency versus the compressive load applied to the metatarsal bone of the test results, which show an increasing slope for the increasingly destabilized testing cases, the increased slope of the curves also corresponding to increased plate maximum principal strain measurements.

FIG. 14 illustrates a graph of resonant frequency versus compressive load applied to the metatarsal showing an increasing slope for the increasingly destabilized testing cases. The increased slope of the curves also corresponds to increased plate maximum principal strain measurements. Test results revealed that the resonant frequency associated with the electromagnetic coupling between the antenna and plate in the plate-bone construct appropriately shifted in each of the three conditions due to the level of stability that was simulated across the plate-bone construct. Accordingly, the resonant frequency shift was greatest for the bicortical osteotomy, followed by the unicortical osteotomy, and the healthy case. The increase in the resonant frequency shift (corresponding to the increased slope of 264 Hz/N for the bicortical osteotomy versus the less slope of 12 Hz/N for the healthy bone) resulted from the increasingly unstable conditions to which the plate-bone construct was applied. These data demonstrate that the frequency shift per applied load can be used to detect and identify the degree to which the bone has been stabilized. This also corresponded to an increase in the maximum principal strain measured on the plate (data derived from the wired strain gauge), showing that as the bone became less stable, the load on the plate increased (higher slope). These data show that this telemetric sensing technology can be used to measure the relative load sharing on the fixation plate itself, and this can be applied to monitor fracture healing without the use of an in-dwelling sensor.

Figure 15:
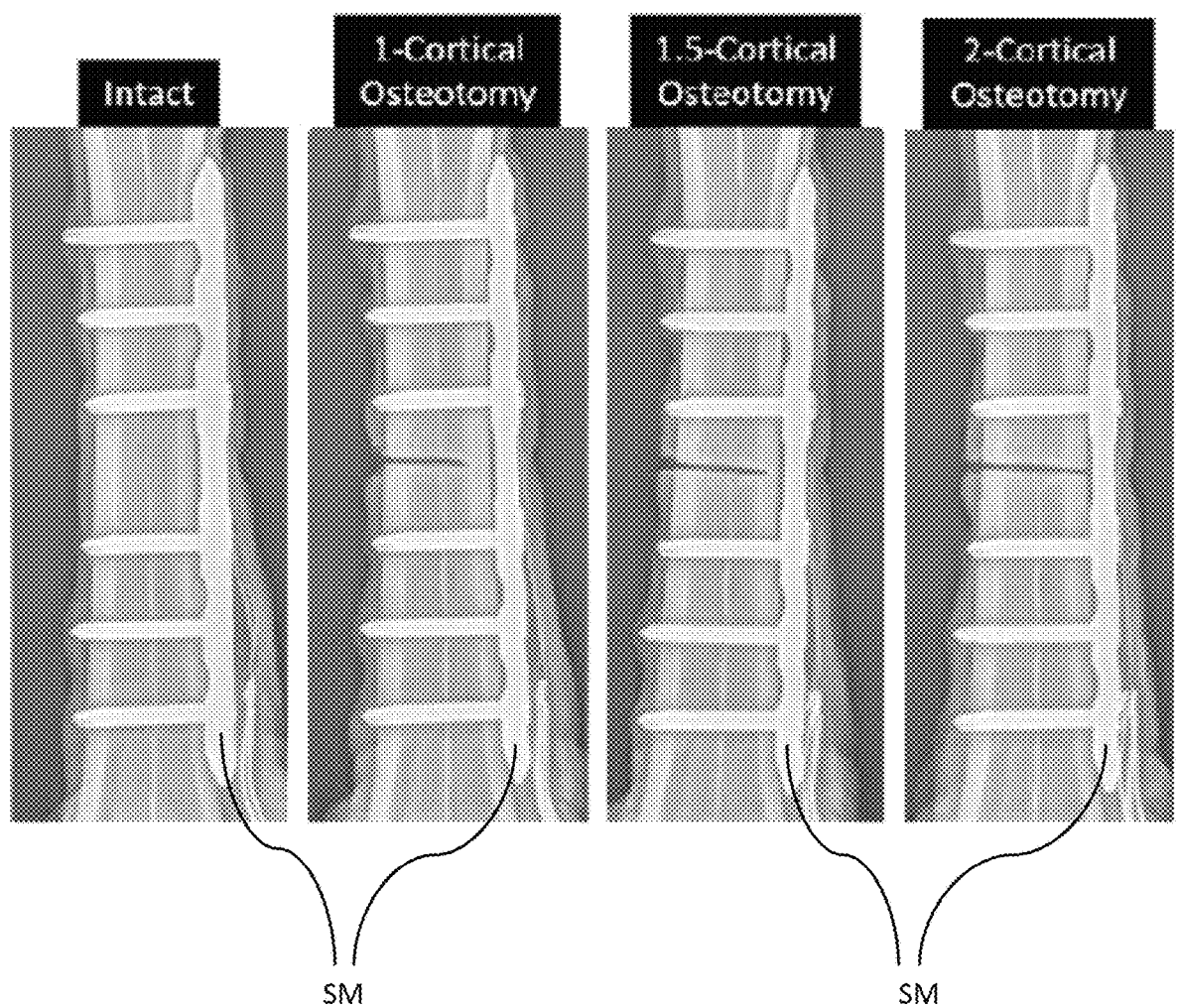
FIG. 15 illustrates radiographs of four different metatarsal bone conditions for the testing in the setup of FIG. 12.
Figure 16:
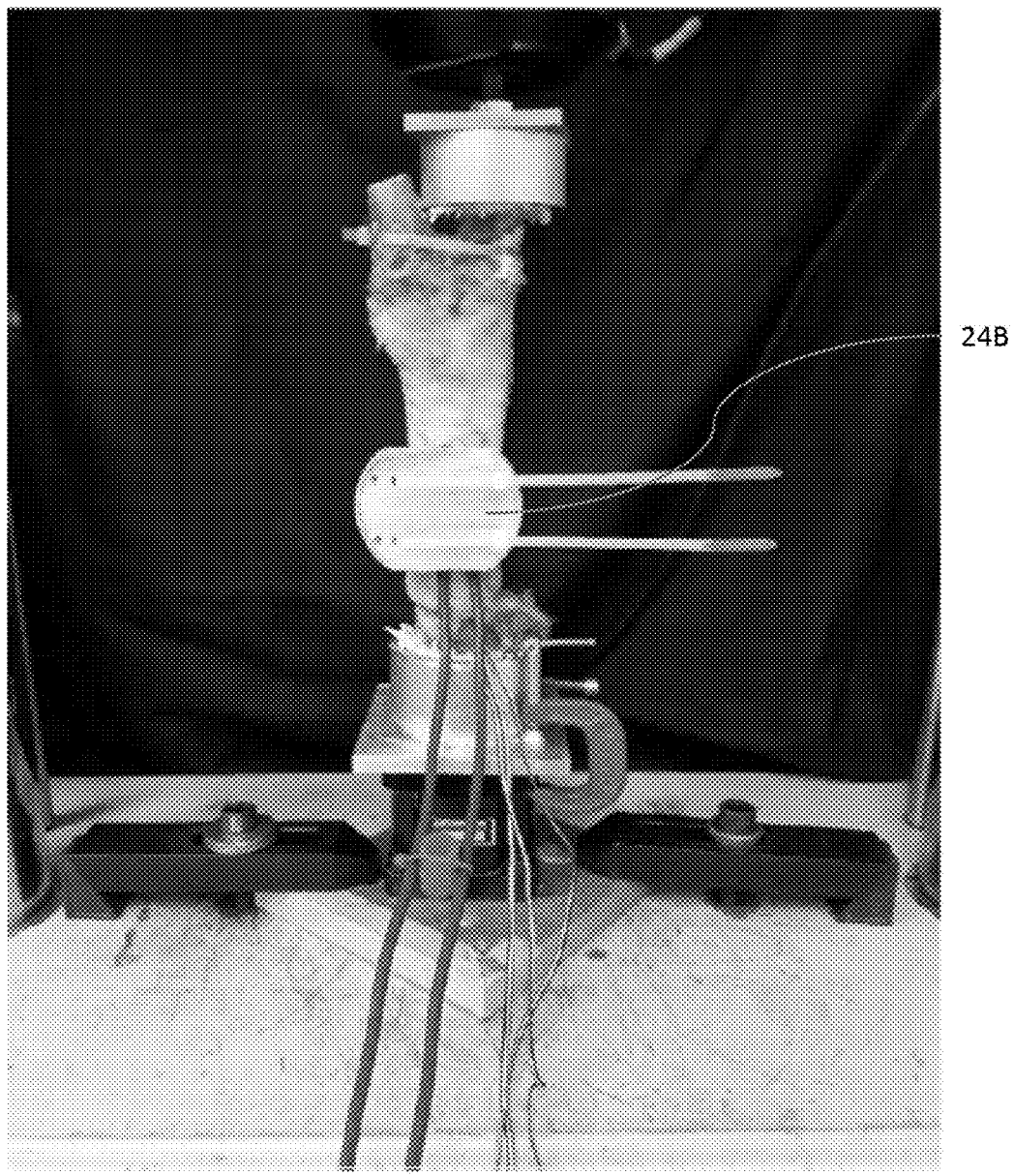
FIG. 16 illustrates the testing setup of FIG. 12 for testing a metatarsal bone illustrated in FIG. 12 with a compression load 0-500N, 5 cycles, with 3 tests for each condition.

FIG. 16 shows a second benchtop experimental setup using sheep metatarsal bone similar to FIG. 12. Here, the center of the fixation plate was instrumented with a wired strain gauge rosette to directly measure the strain on the plate with mechanical loading and generate a resonance frequency versus strain calibration curve. The plate-bone construct was loaded with compression from 0 to 500 N for 5 cycles, with 3 tests for each condition. The same plate-bone construct was tested in four bone conditions to simulate a fracture and the increased stabilization of the bone as a fracture heals. A shown in FIG. 15, these four conditions were healthy (intact), 1-cortical osteotomy (partially destabilized bone), 1.5-cortical osteotomy (further destabilized bone), and 2-cortical osteotomy (full fracture). The test of each condition for each plate-bone construct was repeated six times. For three repetitions, the antenna depicted in FIG. 3 was clamped to the construct, and for the other three repetitions, the antenna depicted in FIG. 4 was clamped to the construct. Between each repetition the antenna was removed and then clamped back in place in order to test the consistency of the test results with respect to the placement of the antenna.

Figure 18:
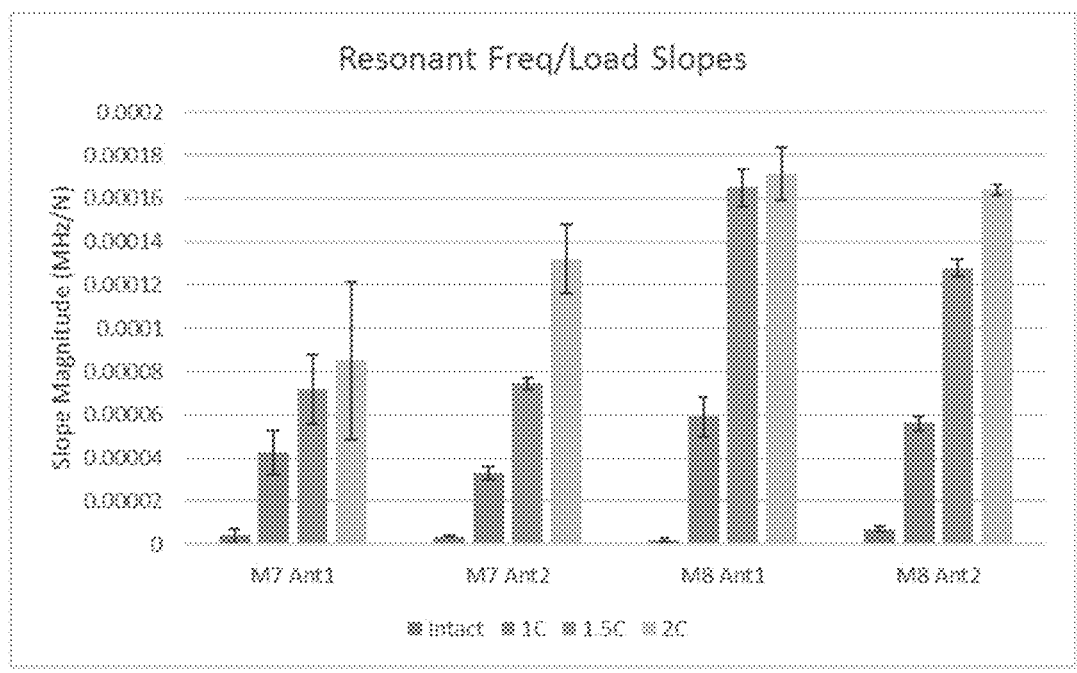
FIG. 18 illustrates the resonant frequency/load slope using the antenna of FIG. 4 and the antenna of FIG. 5.

The experimental results using the methods depicted by FIGS. 15 and 16 and described above are shown in FIGS. 17 and 18. The data shown in FIG. 17 show the mean slopes of the resonant frequency versus applied load curves for two tested plate-bone constructs (M7 and M8). FIG. 18 shows the mean and standard deviations of these data. The results demonstrate an increasing slope magnitude for each progressively destabilized condition. Statistical analyses using student's t-tests conducted individually for each plate-bone construct based on the three repetitions for each antenna showed that statistically significant differences could be detected in the slope magnitude between conditions, indicating that the resonant frequency data from the antenna can be used to detect the relative load carried by the plate (i.e., the destabilization of the plate-bone construct). The antenna depicted in FIG. 4 (Antenna 2) resulted in lower p-values than the antenna depicted in FIG. 3 (Antenna 1).

Given the disclosure of the present invention, one versed in the art would appreciate that there may be other embodiments and modifications within the scope and spirit of the present invention. Accordingly, all modifications attainable by one versed in the art from the present disclosure within the scope and spirit of the present invention are to be included as further embodiments of the present invention. The scope of the present invention accordingly is to be defined as set forth in the appended claims.

What is claimed is:

1. A method of monitoring changes in a structural member (SM) as the SM undergoes at least one of displacement or deformation, the method comprising:
   a disposing step of disposing an antenna spaced from the SM so that a portion of the antenna confronting the SM does not contact the SM at least at no load condition;
   an inducing step of inducing a magnetic or electromagnetic field in the vicinity of the SM to create a coupling of the magnetic or electromagnetic field between the antenna and the SM, where characteristics of the magnetic or electromagnetic field coupling between the antenna and the SM are associated with one of the distance between the SM and the emitting antenna or the deformation state of the SM;
   an outputting step of outputting electrical signals representing the characteristics of the magnetic or electromagnetic field coupling between the antenna and the SM, without using any strain sensing device directly attached to the SM;
   a first determining step of determining the characteristics of the magnetic or electromagnetic field coupling between the antenna and the SM based on the electrical signals; and
   a storing step of storing the determined characteristics of the magnetic or electromagnetic field coupling between the antenna and the SM in a storage device.

2. The method according to claim 1, further comprising:
   a repeating step of repeating the inducing step, the outputting step, the first determining step, and the storing step at a predetermined interval for one of an evaluation period or until a predetermined number of the characteristics of the magnetic or electromagnetic field coupling between the antenna and the SM has been determined.

3. The method according to claim 2, further comprising:
   a second determining step of determining a shift in characteristics of the magnetic or electromagnetic field coupling between the antenna and the SM over the evaluation period or a time lapsed to determine the predetermined number of the characteristics of the magnetic or electromagnetic field coupling between the antenna and the SM.

4. The method according to claim 3, further comprising:
   a third determining step of determining a temporal change in relative displacement or deformation of the SM over the evaluation period or the time lapsed based on the shift determined in the second determining step.

5. The method according to claim 1, wherein the SM is mountable to a target object to be monitored, the SM undergoing the at least one of displacement or deformation as the target structural object undergoes at least one of displacement or deformation.

6. The method according to claim 1, further comprising:
   a loading step of applying a known or measurable force or moment to the SM; and
   an analyzing step of analyzing the determined characteristics in relation to the known or measurable force of moment applied to the SM in the loading step.

7. The method according to claim 5, further comprising:
   a loading step of applying a known or measurable force or moment to the SM; and
   an analyzing step of analyzing the determined characteristics in relation to the known or measurable force of moment applied to the SM in the loading step.

8. The method according to claim 1, wherein:
   the inducing step comprises using the antenna that has at least one wire configured to induce the magnetic or electromagnetic field and output the electrical signals, which is readable by a network analyzer, and
   the at least one wire is connectable to an input port of the network analyzer.

9. The method according to claim 8, wherein the at least one wire comprises a coaxial cable.

10. The method according to claim 1, wherein:
   the inducing step comprises using the antenna that has a first wire configured to induce the magnetic or electromagnetic field; and
   the outputting step comprises using the antenna that further has a second wire configured to output the electrical signals, which is readable by a network analyzer, and the first and second wires are connectable respectively to first and second input ports of the network analyzer.

11. The method according to claim 9, wherein each of the first and second wires comprises a coaxial cable.

12. The method according to claim 4, wherein the change in relative displacement or deformation of the SM over the evaluation period or the lapsed time is represented as a slope of resonant frequency/load.

13. The method according to claim 12, wherein a degree of the slope represents stability, with a higher slope representing a more unstable condition and a less slope representing a more stable condition.

14. A system for monitoring changes in a structural member (SM) as the SM undergoes one of displacement or deformation, the system comprising:
an antenna configured to:
induce, using a first electrical signal, a magnetic or electromagnetic field in the vicinity of the SM to create a coupling of the magnetic or electromagnetic field between the antenna and the SM, where characteristics of the magnetic or electromagnetic field coupling between the antenna and the SM are associated with one of the distance between the SM and the emitting antenna or the deformation state of the SM; and
output a second electrical signal representing the magnetic or electromagnetic field coupling between the antenna and the SM, without using any strain sensing device directly attached to the SM;
an antenna holder configured to hold the antenna at a fixed distance spaced from the SM so that a portion of the antenna confronting the SM does not contact the SM at least at no load condition;
a network analyzer configured to:
output the first electrical signal to the antenna for inducing the magnetic or electromagnetic field;
receive the second electrical signal from the antenna; and
determine the characteristics of the magnetic or electromagnetic field coupling between the antenna and the SM based on the received second electrical signal;
a controller including a memory storing instructions and a processor configured to implement instructions stored in the memory and execute:
a collecting task that stores, in the memory or another storage device, a plurality of characteristics of the magnetic or electromagnetic field coupling between the antenna and the SM determined at a predetermined interval by the network analyzer over an evaluation period;
a first determining task that determines a shift in characteristics of the magnetic or electromagnetic field coupling between the antenna and the SM over the evaluation period; and
a second determining task that determines a temporal change in relative deformation or displacement of the SM over the evaluation period.

15. The system according to claim 14, wherein:
the antenna comprises at least one wire configured to receive the first signal to induce the magnetic or electromagnetic field, and output the second signal, and
the at least one wire is connectable to at least one input port of the network analyzer.

16. The system according to claim 14, wherein:
the antenna comprises a first wire configured to receive the first signal to induce the magnetic or electromagnetic field and a second wire configured to output the second electrical signal, and
the first and second wires are connectable respectively to first and second input ports of the network analyzer.

17. The system according to claim 15, wherein the at least one wire comprises a coaxial cable.

18. The system according to claim 16, wherein each of the first and second wires comprises a coaxial cable.

19. The system according to claim 14, further comprising:
antenna interface including an antenna housing mountable to the SM and the antenna mounted to the housing, and
wherein the second determining task determines the temporal change in relative deformation or displacement of the SM over the evaluation period, which is a predetermined evaluation period, using the second electrical signal.

20. A system for monitoring change in a structural member (SM) as the SM undergoes one of deformation or displacement, the system comprising:
an antenna configured to:
induce, using a first electrical signal, a magnetic or electromagnetic field in the vicinity of the SM to create a coupling of the magnetic or electromagnetic field between the antenna and the SM, where the characteristics of the magnetic or electromagnetic field coupling between the antenna and the SM are associated with one of the distance between the SM and the emitting antenna or the deformation state of the SM; and
output a second electrical signal representing the magnetic or electromagnetic field coupling between the antenna and the SM, without using any strain sensing device directly attached to the SM;
an antenna holder configured to hold the antenna at a fixed distance spaced from the SM so that a portion of the antenna confronting the SM does not contact the SM at least at no load condition;
a controller including a memory storing instructions and a processor configured to implement instructions stored in the memory; and
a hardware interface configured to output the first electrical signal to the antenna and receive the second electrical signal and convert the received electrical signal to a third signal readable by the controller,
wherein the processor is configured to execute:
a first determining task that receives the third electrical signal from the hardware interface and determines characteristics of the magnetic or electromagnetic field coupling between the antenna and the SM based on the third signal;
a repeating task that repeats the first determining task to obtain a plurality of characteristics of the magnetic or electromagnetic field coupling between the antenna and the SM determined by the first determining task at a predetermined interval over an evaluation period;
a second determining task that determines a shift in characteristics of the magnetic or electromagnetic field coupling between the antenna and the SM after each occurrence of the first determining task determining twice the characteristics of the magnetic or electromagnetic field coupling between the antenna and the SM at the predetermined interval, or collectively at the end of the evaluation period; and a third determining task that determines a temporal change in relative deformation or displacement of the SM over the evaluation period.

21. The system according to claim 20, wherein:
the antenna comprises at least one wire configured to receive the first signal to induce the magnetic or electromagnetic field, and output the second signal, and
the at least one wire is connectable to at least one input port of the hardware interface.

22. The system according to claim 20, wherein:
the antenna comprises a first wire configured to receive the first signal to induce the magnetic or electromagnetic field and a second wire configured to output the second electrical signal, and
the first and second wires are connectable respectively to first and second input ports of the hardware interface.

23. The system according to claim 21, wherein the at least one wire comprises a coaxial cable.

24. The system according to claim 22, wherein each of the first and second wires comprises a coaxial cable.

25. The system according to claim 20, further comprising:
antenna interface including an antenna housing mountable to the SM and the antenna mounted to the housing, and
wherein the third determining task determines the temporal change in relative deformation or displacement of the SM over the evaluation period, which is a predetermined evaluation period, using the second electrical signal.

26. An apparatus for monitoring change in a structural member (SM) as the SM undergoes one of deformation or displacement, using an antenna configured to:
induce, using a first electrical signal, a magnetic or electromagnetic field in the vicinity of the SM to create a coupling of the magnetic or electromagnetic field between the antenna and the SM, where the characteristics of the magnetic or electromagnetic field coupling between the antenna and the SM are associated with one of the distance between the SM and the emitting antenna or the deformation state of the SM; and
output a second electrical signal representing the magnetic or electromagnetic field coupling between the antenna and the SM into a second electrical signal, without using any strain sensing device directly attached to the SM,
wherein the apparatus comprises:
a controller including a memory storing instructions and a processor configured to implement instructions stored in the memory; and
a hardware interface configured to output the first electrical signal to the antenna and receive the second electrical signal and convert the received electrical signal to a third signal readable by the controller,
wherein the processor is configured to execute:
a first determining task that receives the third electrical signal from the hardware interface and determines the characteristics of the magnetic or electromagnetic field coupling between the antenna and the SM based on the third electrical signal;
a repeating task that repeats the first determining task to obtain a plurality of characteristics of the magnetic or electromagnetic field coupling between the antenna and the SM determined by the first determining task at a predetermined interval over an evaluation period;
a second determining task that determines a shift in characteristics of the magnetic or electromagnetic field coupling between the antenna and the SM after each occurrence of the first determining task determining twice the characteristics of the magnetic or electromagnetic field coupling between the antenna and the SM at the predetermined interval, or collectively at the end of the evaluation period; and
a third determining task that determines a temporal change in relative deformation or displacement of the SM over the evaluation period.

* * * * *